(12) United States Patent
Mitchell et al.

(10) Patent No.: US 6,709,465 B2
(45) Date of Patent: Mar. 23, 2004

(54) RADIALLY EXPANDING URETERAL DEVICE

(75) Inventors: Michael Edward Mitchell, Brookline, MA (US); Gloria Miran Ro, Quincy, MA (US); Aoy Tomita, Brookline, MA (US)

(73) Assignee: Fossa Medical, Inc., Boston, MA (US)

( * ) Notice: Subject to any disclaimer, the term of this patent is extended or adjusted under 35 U.S.C. 154(b) by 0 days.

(21) Appl. No.: 09/755,487

(22) Filed: Jan. 5, 2001

(65) Prior Publication Data

US 2001/0021835 A1 Sep. 13, 2001

Related U.S. Application Data

(63) Continuation-in-part of application No. 09/272,660, filed on Mar. 18, 1999, now Pat. No. 6,214,037.

(51) Int. Cl.$^7$ ................................. A61F 2/04
(52) U.S. Cl. ............... 623/23.7; 623/1.15; 623/1.3; 623/1.16; 606/127
(58) Field of Search ................. 623/1.15, 1.16, 623/1.18, 1.3, 1.31, 1.37, 23.64, 23.66, 23.7, 901; 606/200, 127

(56) References Cited

U.S. PATENT DOCUMENTS

| | | | | |
|---|---|---|---|---|
| 3,108,593 A | * | 10/1963 | Glassman | 128/328 |
| 3,108,594 A | * | 10/1963 | Glassman | 128/328 |
| 4,531,933 A | | 7/1985 | Norton et al. | 604/8 |
| 4,874,360 A | | 10/1989 | Goldberg et al. | 604/8 |
| 4,950,227 A | | 8/1990 | Savin et al. | 604/8 |
| 4,973,301 A | | 11/1990 | Nissenkorn | 604/8 |
| 5,129,910 A | | 7/1992 | Phan et al. | 606/127 |
| 5,246,445 A | * | 9/1993 | Yachia et al. | 606/108 |
| 5,380,270 A | | 1/1995 | Ahmadzadeh | 604/9 |
| 5,380,335 A | | 1/1995 | Dormia | 606/127 |

(List continued on next page.)

OTHER PUBLICATIONS

Foster, Pub. No. US 2001/0041899 A1, application No. 09/277,098, filed Mar. 26, 1999, priority date Mar. 27, 1998, Minimally–Invasive Medical Retrieval Device.*
Desai, Pub. No. US 2003/0135268 A1, Pub. Date: Jul. 17, 2003, Application No. 09/547,708, Secure Stent For Maintaining a Lumenal Opening.*
Shalev et al., Pub. No. US 2003/0097172 A1, Pub. Date: May 22, 2003, Application No. 10/239,980, Narrowing Implant.*
International Search Report, PCT Application Ser. No. PCT/US01/24409.

*Primary Examiner*—Bruce Snow
*Assistant Examiner*—Cheryl Miller
(74) *Attorney, Agent, or Firm*—Foley Hoag, LLP (57) ABSTRACT

A ureteral device is provided for facilitating stone passage through a ureter or duct. An exemplary ureteral device includes a flexible, elongate body that defines a plurality of cages along the body. In a contracted state the cages have a reduced diameter. When an activation force is applied, the cages transform to an expanded state, thereby defining a plurality of void spaces. The void spaces are configured to receive an obstruction, such as a stone. The ureteral device can then be induced to the contracted state to compress the obstruction within the elongate, flexible body and then be removed from the obstructed passage. The ureteral device can be configured to have different numbers of elongate flexible members that define the cages.

37 Claims, 5 Drawing Sheets

U.S. PATENT DOCUMENTS

| | | | | |
|---|---|---|---|---|
| 5,401,257 A | * | 3/1995 | Chevalier, Jr. et al. | 604/265 |
| 5,454,365 A | * | 10/1995 | Bonutti | 600/204 |
| 5,496,330 A | | 3/1996 | Bates et al. | 606/127 |
| 5,518,498 A | * | 5/1996 | Lindenberg et al. | 600/30 |
| 5,551,954 A | | 9/1996 | Buscemi et al. | 623/1 |
| 5,599,291 A | | 2/1997 | Balbierz et al. | 604/8 |
| 5,647,843 A | | 7/1997 | Mesrobian et al. | 604/8 |
| 5,658,296 A | | 8/1997 | Bates et al. | 606/127 |
| 5,681,274 A | | 10/1997 | Perkins et al. | 604/8 |
| 5,746,745 A | | 5/1998 | Abele et al. | 606/108 |
| 5,755,781 A | * | 5/1998 | Jayaraman | 623/1.1 |
| 5,776,142 A | | 7/1998 | Gunderson | 606/108 |
| 5,776,162 A | * | 7/1998 | Kleshinski | 606/198 |
| 5,788,710 A | | 8/1998 | Bates et al. | 606/127 |
| 5,792,145 A | | 8/1998 | Bates et al. | 606/127 |
| 5,795,319 A | | 8/1998 | Ali | 604/8 |
| 5,814,006 A | * | 9/1998 | Planz | 604/8 |
| 5,817,152 A | | 10/1998 | Birdsall et al. | 623/1 |
| 5,824,037 A | | 10/1998 | Fogarty et al. | 623/1 |
| 5,830,217 A | | 11/1998 | Ryan | 606/108 |
| 5,868,783 A | * | 2/1999 | Tower | 606/198 |
| 5,873,907 A | | 2/1999 | Frantzen | 623/1 |
| 5,885,258 A | * | 3/1999 | Sachdeva et al. | 604/281 |
| 5,902,332 A | * | 5/1999 | Schatz | 623/1.3 |
| 5,911,732 A | | 6/1999 | Hojeibane | 606/194 |
| 5,944,728 A | | 8/1999 | Bates | 606/127 |
| 5,984,963 A | | 11/1999 | Ryan et al. | 623/12 |
| 5,989,266 A | | 11/1999 | Foster | 606/127 |
| 6,066,168 A | | 5/2000 | Lau et al. | 623/1.16 |
| 6,099,534 A | | 8/2000 | Bates et al. | 606/127 |
| 6,120,534 A | * | 9/2000 | Ruiz | 623/1.19 |
| 6,159,220 A | | 12/2000 | Gobron et al. | 606/127 |
| 6,159,230 A | | 12/2000 | Samuels | 606/200 |
| 6,168,603 B1 | | 1/2001 | Leslie et al. | 606/114 |
| 6,183,482 B1 | | 2/2001 | Bates et al. | 606/127 |
| 6,197,047 B1 | * | 3/2001 | Kranz | 623/1.15 |
| 6,224,612 B1 | * | 5/2001 | Bates et al. | 606/114 |
| 6,254,571 B1 | * | 7/2001 | Hart | 604/107 |
| 6,258,118 B1 | * | 7/2001 | Baum | 623/1.19 |
| 6,264,664 B1 | | 7/2001 | Avellanet | 606/128 |
| 6,267,775 B1 | * | 7/2001 | Clerc et al. | 606/198 |
| 6,312,463 B1 | * | 11/2001 | Rourke et al. | 623/1.39 |
| 6,319,261 B1 | | 11/2001 | Bowers | 606/127 |
| 6,325,825 B1 | * | 12/2001 | Kula | 623/1.3 |
| 6,344,055 B1 | * | 2/2002 | Shukov | 623/1.15 |
| 6,395,021 B1 | | 5/2002 | Hart et al. | 623/1.15 |
| 2003/0097172 A1 | | 5/2003 | Shalev et al. | 623/1.31 |
| 2003/0135268 A1 | | 7/2003 | Desai | 623/1.19 |

* cited by examiner

RADIALLY EXPANDING URETERAL DEVICE

CROSS REFERENCE TO RELATED APPLICATIONS

This application is a continuation-in-part of U.S. application Ser. No. 09/272,660, filed Mar. 18, 1999 now U.S. Pat. No. 6,214,037.

STATEMENT REGARDING FEDERALLY SPONSORED RESEARCH

Not applicable.

FIELD OF THE INVENTION

The present invention relates to a medical device, and more particularly to a medical device for facilitating passage and/or removal of kidney stones.

BACKGROUND OF THE INVENTION

Calculus or stones in the urinary tract or kidneys usually arise because of the breakdown of a delicate balance in the body. Specifically, the kidneys must conserve water to function, but they must excrete materials that have a low solubility. These opposing requirements must be balanced during adaptation to diet, climate and activity. The problem is mitigated to some degree because urine contains substances that inhibit crystallization of stone forming minerals. However, when urine becomes supersaturated with insoluble materials, because excretion rates are excessive and/or because water conservation is extreme, crystals form and may grow and aggregate to form a stone.

Although small crystals are readily voided from the kidney with urine, the larger stones frequently become dislodged from the kidney and enter the ureter or occlude the uretero-pelvic junction, causing pain and obstruction. Although some stones can ultimately traverse the ureter, their passage usually produces pain and bleeding. Usually the pain is so severe that narcotic drugs are needed for its control.

Removal of stones from the kidneys or urinary tract can be effected medically or surgically. A well known surgical approach involves passing a flexible basket in a retrograde manner up the ureter from the bladder, and using the basket to capture the stones. Another surgical technique, known as extracorporeal lithotripsy, entails transmission of high-intensity shock waves from outside the body to fragment the stones within the body. The resulting stone fragments are then voided with urine. Yet another surgical technique, percutaneous ultrasonic lithotripsy, requires the passage of a rigid cystoscopy-like instrument in the renal pelvis through a small incision in the flank whereupon stones are broken up by a small ultrasound transducer and removed directly. Another surgical technique is laser lithotripsy via a uretero-scope. All of these procedures, which can be quite painful, are elaborate and expensive, and do not always result in complete removal of the stones and fragments.

Stents are used to decompress ureteral obstruction, ensuring that urine drains from the kidney to the bladder. It has also been recognized that placement of a stent within the ureter can help small stones and stone fragments to transit the ureter. In a typical procedure involving a stent, a guide wire is passed through the ureter to the renal pelvis. A hollow, flexible, cylindrical stent is then advanced with a pusher over the guide wire. The guide wire and pusher are then extracted from the stent and the body, leaving an open lumen for urine to pass through. However, because the lumen defined by the cylindrical stent is even smaller than the ureter itself, all but the smallest stones and sludge are precluded from passing therethrough. Some fragments are able to pass around the ureteral stent but larger stone fragments are unable to pass. In many cases, stone fragments often block the open stent passageway.

SUMMARY OF THE INVENTION

The present invention provides an improved ureteral device that is not only well-suited for decompressing an obstructed passage within the body such as a ureter, but which is also configured to gently dilate and thus facilitate stone passage through a ureter or duct.

In an exemplary embodiment a ureteral device includes a flexible, elongate body that defines an open channel along the body. At least a portion of the body is made of a resilient material, wherein the open channel defines a void volume. A retaining or compressive force applied to the resilient material causes the void volume to be reduced, or maintained in a reduced state, until the retaining or compressive force is removed or maintained in a reduced state, until the retaining or compressive force is removed. A sleeve, a wire, or an adhesive soluble in liquid or dissolvable by ultrasound can provide the retaining force.

In some embodiments, a flexible, elongate body includes elements distributed along the body and that are movable from a first state to a second state to increase the diameter of the ureteral device from a first diameter to a second diameter.

In another embodiment, a flexible, elongate body defines a plurality of flexible elongate members which in turn define a plurality of cages. The cages are movable from a cage contracted state to a cage expanded state.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIGS. 2–9D are detailed views of end portions of ureteral devices in accordance with present invention;

DETAILED DESCRIPTION OF THE INVENTION

Figure 1:
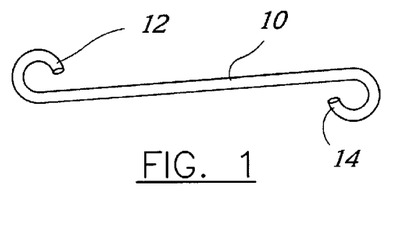
FIGS. 1 is a perspective view of a ureteral device in accordance with the present invention.

FIG. 1 is a perspective view of a ureteral device in accordance with the invention. The ureteral device includes a body 10 having a first end portion 12 and a second end portion 14. The ureteral device body and end portions are flexible enough to assume a substantially linear configuration. However, in a static state, the end portions of the ureteral device can assume a curved orientation as shown. Details regarding the features, exemplary dimensions, and use of the ureteral device follow.

Figure 2:
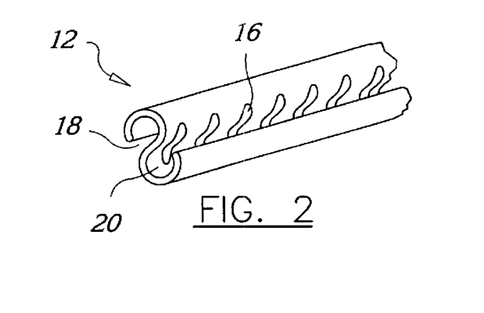

FIG. 2 is a detailed view of a straightened first end portion 12 of an exemplary ureteral device. The opposite, second end portion 14 (not shown in FIGS. 2–8) is substantially identical to the first end portion. In this view, the ureteral device body and end portions have an "S" shaped cross-section. Apertures are provided along all or a portion of the length of the ureteral device. Although the apertures 16 are shown as being elongate, they can also be oval or circular. The "S" shape of the ureteral device body and end portions defines two longitudinal channels 18 and 20. As used herein, a channel is a path defined, or at least partially bound, by a portion of the ureteral device body or end portions.

Figure 3:
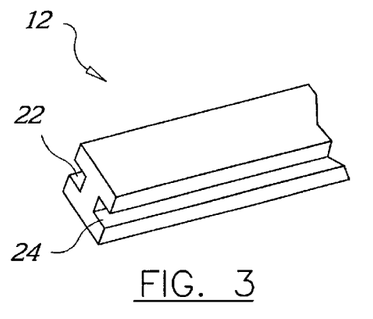

FIG. 3 illustrates the ureteral device in an "I" configuration. Although not illustrated other than FIG. 2, apertures can be provided in this and all other ureteral device configurations. The "I" shape defines two longitudinal channels 22 and 24.

Figure 4:
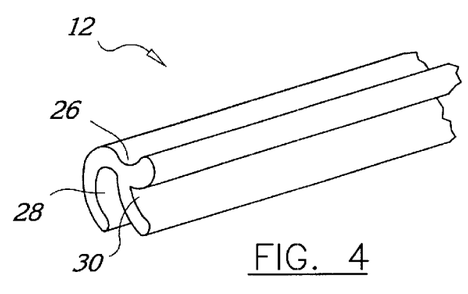

FIG. 4 illustrates the ureteral device configured to provide three channels 26, 28 and 30.

Figure 5:
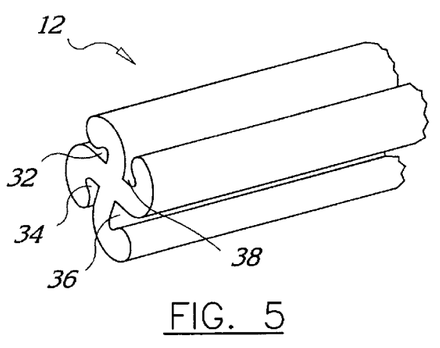

FIG. 5 illustrates the ureteral device configured to provide four channels 32, 34, 36 and 38.

Figure 6:
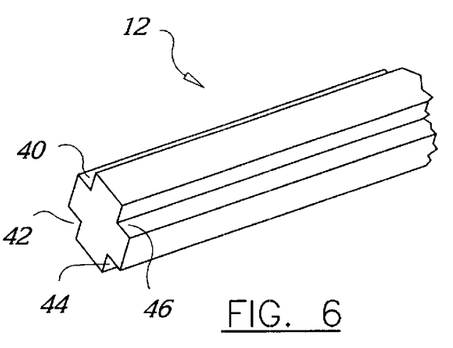

FIG. 6 also depicts the ureteral device that defines four channels 40, 42, 44 and 46.

Figure 7:
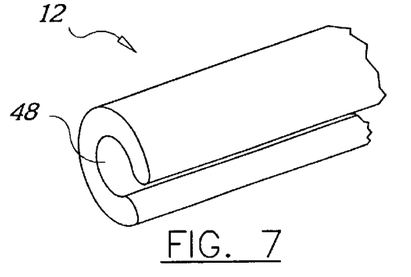

FIG. 7 depicts a ureteral device with a single channel 48.

Figure 8:
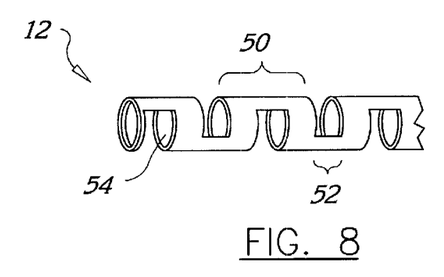

FIG. 8 illustrates a ureteral device having segments 50 joined by linking regions 52 and defining a channel 54. In one embodiment, the linking regions bias or urge adjacent segments away from coaxial alignment. Thus, the channel(s) need not be linear and can be somewhat discontinuous or multiple channels are provided.

Figure 9A:
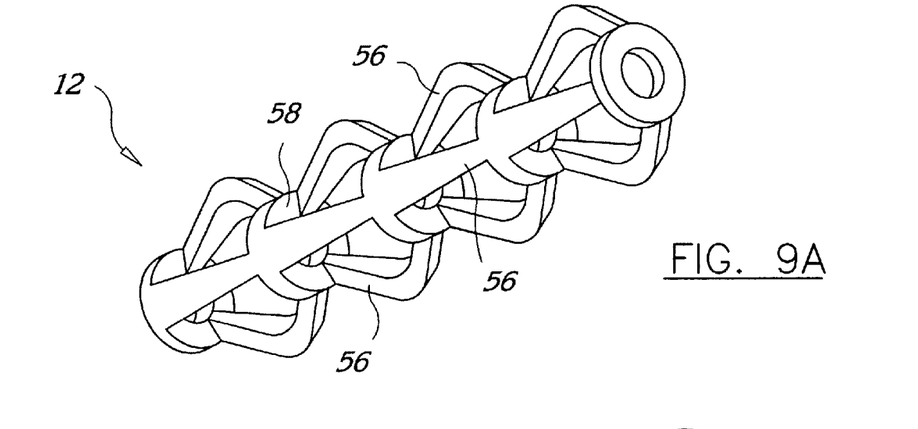
Figure 9B:
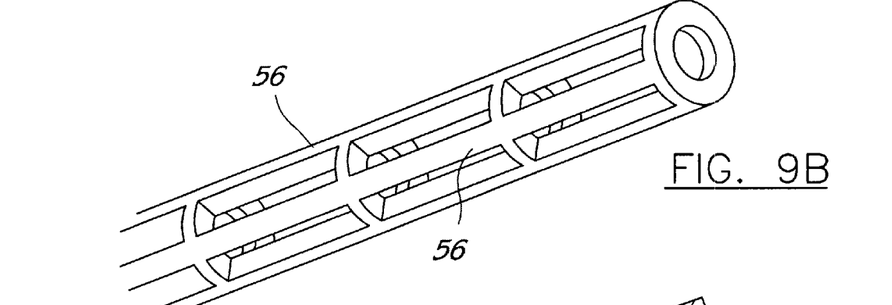
Figure 9C:
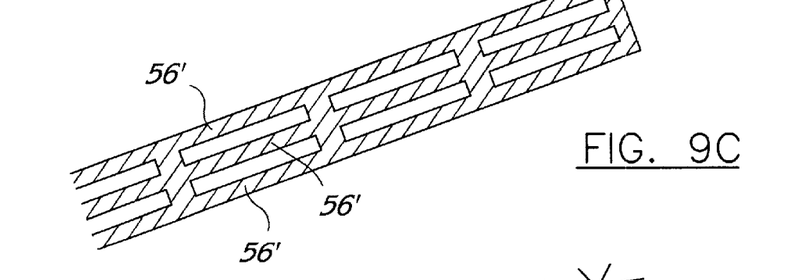
Figure 9D:
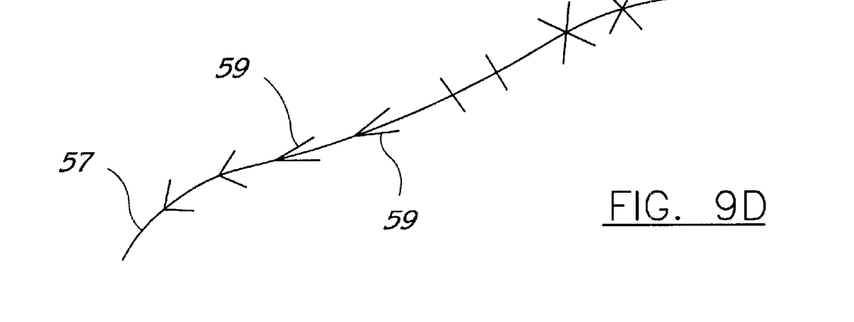

FIG. 9A illustrates a ureteral device having resilient, substantially-longitudinal elements 56. In the illustration, the elements 56 are bowed outward from a central axis of the ureteral device, in a cage expanded state, to provide the ureteral device with an undulating surface and alternating larger and smaller localized circumferential regions. FIG. 9B illustrates the ureteral device of FIG. 9A with the elements 56 in a substantially linear or non-bowed configuration, a cage contracted state. FIG. 9C depicts yet another embodiment of the ureteral device, wherein the ureteral device is substantially planar in a first configuration as shown. In the cage expanded state, elements 56' bow outward as shown with respect to the ureteral device of FIG. 9A. FIG. 9D illustrates yet another embodiment, wherein an elongate flexible body is provided with barbs 59 that can be transitioned from a reduced diameter configuration 59 to a larger diameter configuration. In the illustration, barbs 59 are shown in different configurations and states. The ureteral devices of FIGS. 9A-D can be transitioned from a uniform/reduced diameter configuration to a nonuniform/larger diameter configuration by compressing the ureteral device longitudinally, or by removing a restraining force from outwardly biased elements 56 or 56'. In exemplary embodiments a restraining force is provided by a sleeve as shown with respect to FIG. 10 or with adhesives as described below with respect to FIG. 11.

Figure 10:
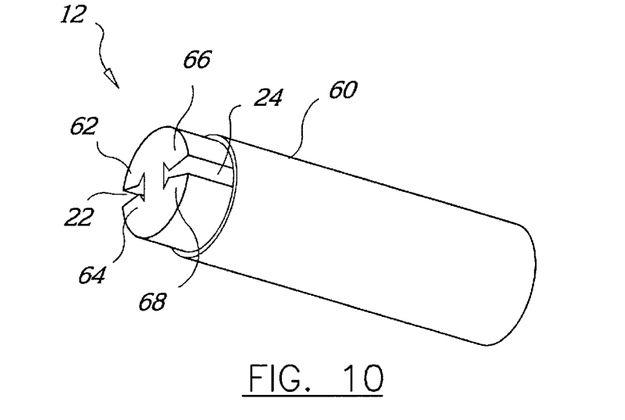
FIG. 10 illustrates the ureteral device of FIG. 3 compressed within a sleeve.

FIG. 10 depicts the ureteral device of FIG. 3 within a sleeve 60. Because at least a portion of the ureteral device is flexible, such as body portions 62, 64, 66 and 68 that define the channels 22 and 24, the ureteral device can be folded into a sleeve having a smaller diameter than the ureteral device in its unfolded state. If the material of the ureteral device is compressible, the ureteral device can be placed into an even smaller diameter sleeve. The sleeve 60 thus can serve at least two important functions: it temporarily reduces the diameter of the ureteral device and, until removal, it provides a smooth exterior surface. Both of these features facilitate deployment of the ureteral device as described below.

Figure 11:
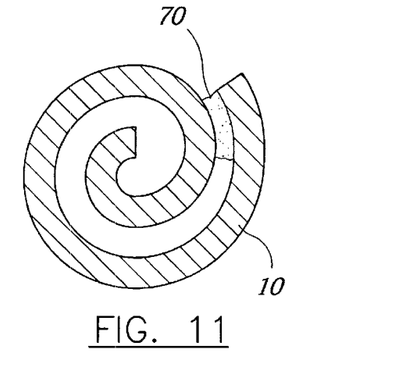
FIG. 11 shows the ureteral device of FIG. 7 held in a compressed state with an adhesive.

Alternatively, as shown in FIG. 11, the ureteral device in a configuration such as shown in the sectional end view of FIG. 7 can be folded or rolled and held in that configuration with a water or acid soluble adhesive 70. Thus, when the adhesive dissolves; the ureteral device unfolds or unrolls.

Exemplary ureteral devices are made of silicone and have lengths in the range of 22 to 32 centimeters for adults and about 16 to 18 centimeters for children. However, the length of the ureteral device can be modified as required. A ureteral device can have a diameter of about 7.0 FR for placement within a ureteral orifice 3 millimeters in diameter. Ureteral devices as described herein are well suited for removal of a stone up to 10 millimeters in diameter.

Figure 12:
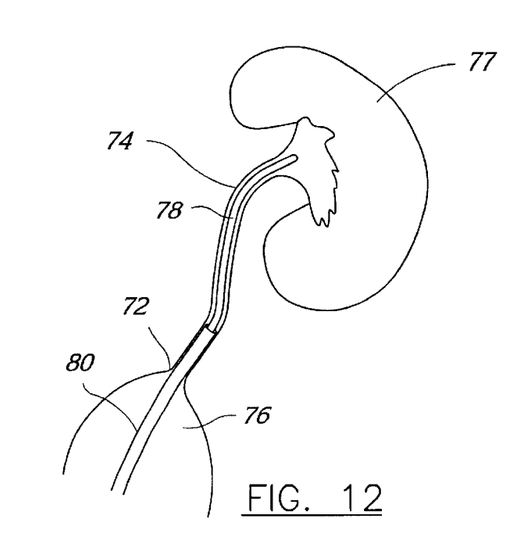
FIG. 12 depicts a step in a procedure for placing a ureteral device in accordance with the invention.

FIG. 12 illustrates a step of an exemplary procedure, wherein a cystoscope has been used to find the orifice 72 of the ureter 74 leading between the bladder 76 and a kidney 77. A flexible wire 78, such as is known in the art, has been guided through the orifice 72 and into the ureter. A ureteral device 80 in accordance with the invention is selected, placed over the wire 78, and passed into the ureter 74.

Figure 13:
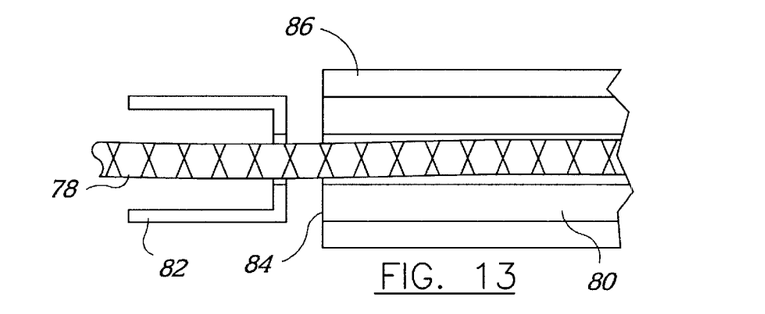
FIG. 13 illustrates the ureteral device and associated components.

As illustrated in FIG. 13, a pusher 82 can be placed over the wire 78 and pressed against the proximal end 84 of the ureteral device 80. In this illustration, the ureteral device 80 is compressed within a sleeve 86.

Figure 14:
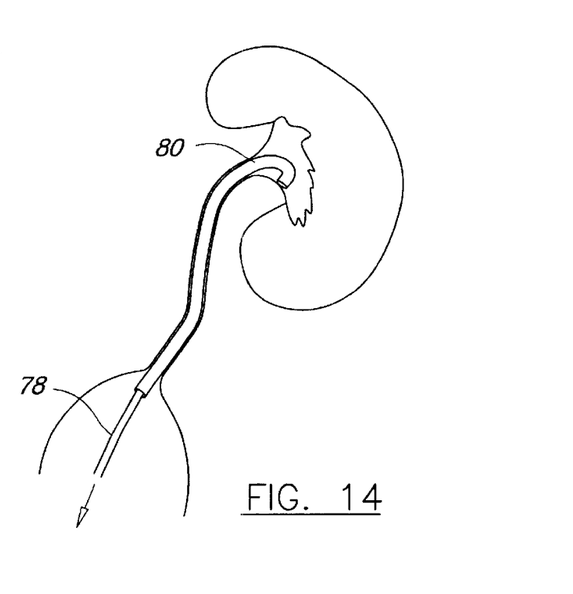
FIG. 14 shows removal of a guidewire from the ureteral device.

The pusher 82, if used, and the flexible wire 78 are then removed, as shown in FIG. 14, and the ureteral device is left in place. If a sleeve is used, it can also be removed from the ureteral device. However, as removal of a sleeve from a ureteral device can be difficult, especially if the ureteral device or portions thereof are compressed by the sleeve, the present invention provides a sleeve that degrades or dissolves to release the ureteral device therefrom. In an exemplary embodiment, the sleeve is made of a material that dissolves in urine within a few hours. The material can be a water, base or acid soluble material such as sugars, polydioxanone, polyglecaprone 25, polyglactine, gelatine sponge, hylauronan-benzyl 15 ester hyaluronic acid, cyanoacrylate, chromic suture material and polyglycolic acid. Additionally, the material can be dissolvable by ultrasound.

Figure 15:
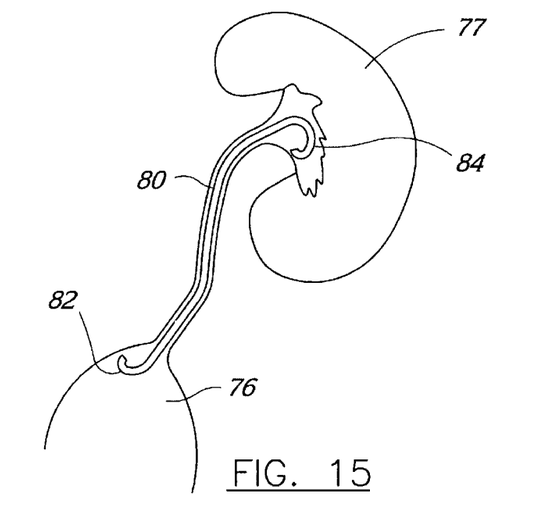
FIG. 15 illustrates the ureteral device in position within a dilated ureter.

When the wire and sleeve are removed, the relatively unconfined ends of the ureteral device form a retention shape, such as by curling to form a "double-J," as is known in the art, and as shown in FIG. 15. A first curled end portion (or "J") anchors a first end 82 of the ureteral device 80 within the bladder 76 and a second curled end portion anchors a second end 84 of the ureteral device within the kidney 77.

Figure 16:
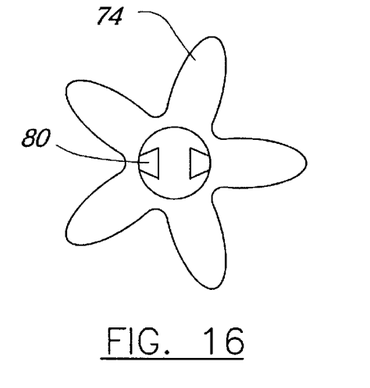
FIG. 16 illustrates a ureteral device within an undilated ureter.
Figure 17:
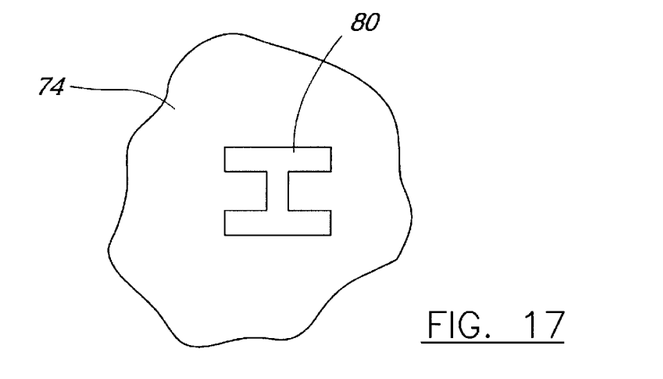
FIG. 17 illustrates the ureteral device of FIG. 16, after the ureter has dilated.

When the ureteral device 80 is in place, the ureter 74 dilates around the ureteral device naturally from a normal state as shown in FIG. 16 to an increased diameter or dilated state as illustrated in FIG. 17. The effect is particularly evident when the ureteral device selected for insertion is a radially expandable ureteral device. Although a stone may not have been able to pass through an undilated ureter, after dilation the stone (depending on its size) is able to pass through the increased diameter ureter. After the stone(s) have been eliminated from the body, the ureteral device is removed from the body. Any stones trapped in the channel(s) are removed with the ureteral device. The channel(s) help to maximize a flow path for urine and they provide an enlarged path for the stones to wash into the bladder. By contrast with known cylindrical ureteral devices, the open cross-section of the present ureteral device is not easily clogged. Furthermore, the open channel configurations do not readily become pinched closed as do known complete, cylindrical, catheter-like tubes.

Instead of removing the ureteral device using techniques known to those skilled in the art, the ureteral device can be fabricated from a material that degrades into small pieces or dissolves so that it can be passed with urine. The ureteral device can be made of a urine, water, acid, or base soluble material such as sugar, polydioxanone, polyglecaprone 25, polyglactine, gelatine sponge, hyaluronan-benzyl ester hyaluronic acid, or cyanoacrylate. Alternatively, the ureteral device can dissolve when exposed to ultrasound. An exemplary ureteral device dissolves completely within a week or two. Even if dissolution of the ureteral device begins when the sleeve is removed, the rate of deterioration is slow enough so that the ureteral device will perform its intended purpose.

In addition to placement in a ureter, the ureteral device in accordance with the invention can be therapeutically effective with respect to obstruction, stricture and external compression of any tubular structure within the body including airways, bile ducts, pancreatic ducts, the bowel, blood vessels and the urethra.

Figure 18:
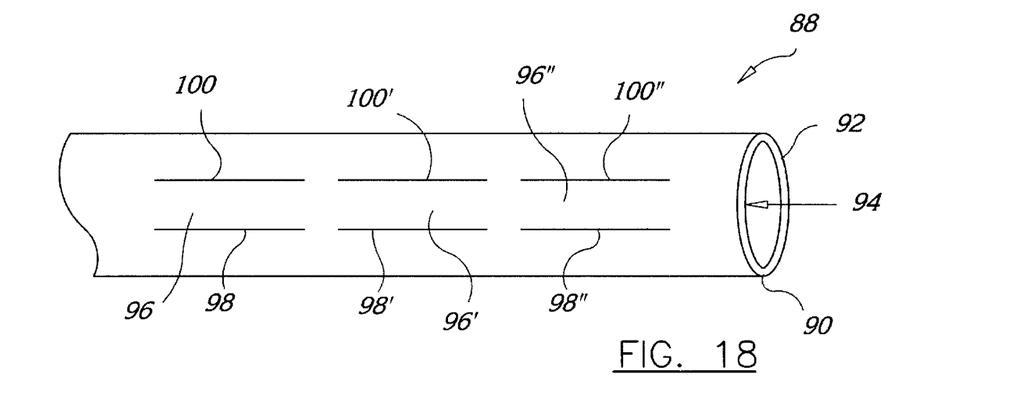
FIG. 18 is a perspective view of a ureteral device in accordance with the present invention, shown in a contracted state.

FIG. 18 is perspective view of another embodiment of a ureteral device similar to the device shown in FIG. 9A. The ureteral device has a body 88 which includes a flexible tube 90, a body wall 92 with an outer surface and an inner surface that define a lumen 94. The body wall 92 has a plurality of elongate flexible members, here exemplified by representative members, 96, 96', 96". The elongate flexible members are arranged in groups of three radially-spaced members. The length of the elongate flexible members can be from slightly less than the full length of the body to less than 1 cm. In some embodiments, the length of the members is from 0.1 cm to 10.0 cm and in other embodiments, the length of the members is from 1.0 cm to 5.0 cm. Further, in some embodiments the lengths of the members is from 2.0 cm to 3.0 cm. The length of the members may vary with the requirements of a given procedure or the size of an obstruction.

Along the members 96, 96', 96" are apertures 98, 98', 98" and apertures 100, 100', 100", which separate members from their adjacent neighboring members. Although the apertures are shown as being elongate, they can also be oval, circular or may be slot-like as shown in FIG. 9. When in a contracted state, the distance between the elongate members and their adjacent neighbors range from completely touching to not touching at all. Also as shown in FIG. 18, when the members are in a contracted state, the body 88 has a substantially uniform diameter with a smooth exterior surface.

Figure 19:
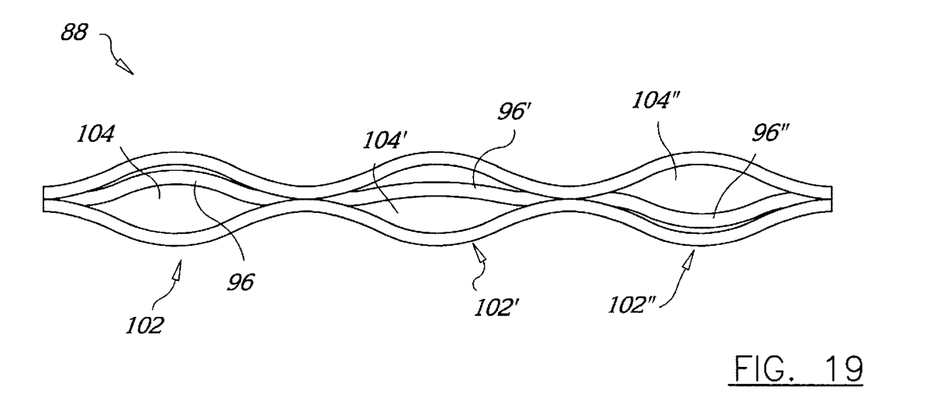
FIG. 19 is a perspective view of the ureteral device of FIG. 18, shown in an expanded state.

Turning now to FIG. 19, the ureteral device of FIG. 18 is shown in an expanded state. When in the expanded state, the elongate flexible members 96, 96", 96" arc away from each adjacent elongate flexible member thereby defining a plurality of cages 102, 102', 102" and void spaces 104, 104'and 104" along the body 88. In the expanded state, the elongate flexible members are in a spaced-apart relation with regard to adjacent elongate flexible members. While these figures show three elongate flexible members per cage, it will be readily understood that various numbers of members may be employed. For example, FIG. 20 shows a ureteral device with four elongate flexible members per cage in an expanded state.

Figure 20:
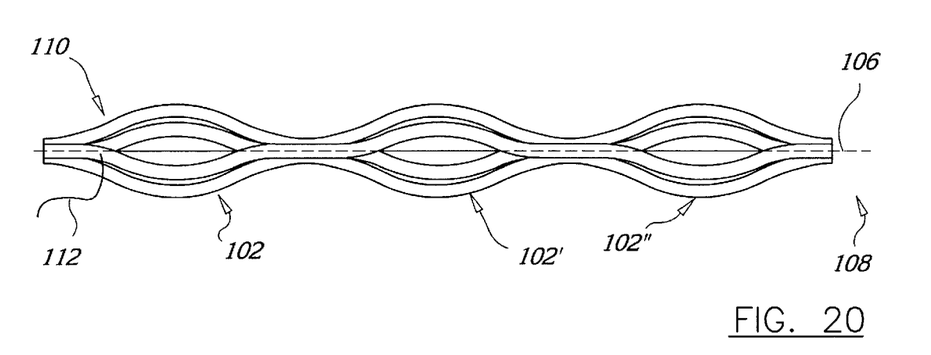
FIG. 20 is a perspective view of a ureteral device in accordance with the present invention, shown in an expanded state.

The cages can be transitioned from a contracted state, as shown in FIG. 18, to an expanded state, as shown in FIGS. 19 and 20. One way that this can be accomplished is by shortening the length of the body 88. For example, by pushing one or both ends of the body 88 axially to shorten the distance between the two ends. Alternatively, a filament 106 can be provided that is secured to a distal region 108 of the body 88 as shown in FIG. 20, wherein pulling the filament toward the proximal end 110 of the body 88 shortens the body causing the members to bow outward and form cages 102, 102' and 102". To prevent the filament 106 from obstructing the cages, the filament can be pulled free of the distal region 108 once sufficient force has been applied to deform flexible members that define the cage.

Another way to facilitate the transition of the cages from one state to the other, is to construct the cages so that they are biased to take an expanded state. The cages are then held in a contracted state by a restraining force as described in more detail above (e.g. sheaths or adhesives). Once the restraining force is removed, the cage will expand to expose the void spaces. When removal of the device is desired, the proximal end of the device or a tether secured thereto can be pulled. An exemplary tether 112 is shown in FIG. 20. In this embodiment, when the tether 112 is pulled, the device will transition from the expanded state to the contracted state. The pulling of one end of the device acts to lengthen the body, thereby contracting the cages.

When the ureteral device is in the contracted state it has a cage diameter that is less than a cage diameter when the device is in the expanded state. The diameter in the contracted state can range from 1 mm to 5 mm and the diameter in the expanded state can range from 5 mm to 20 mm.

Figure 21:
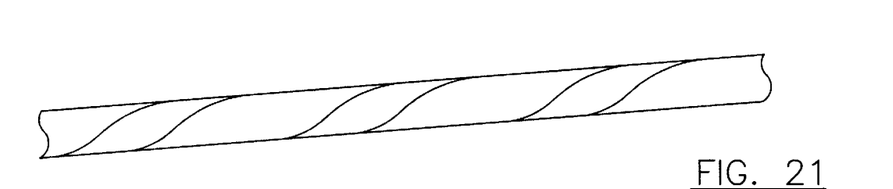
FIG. 21 is a perspective view of a ureteral device in accordance with the present invention, shown in a contracted state.
Figure 22:
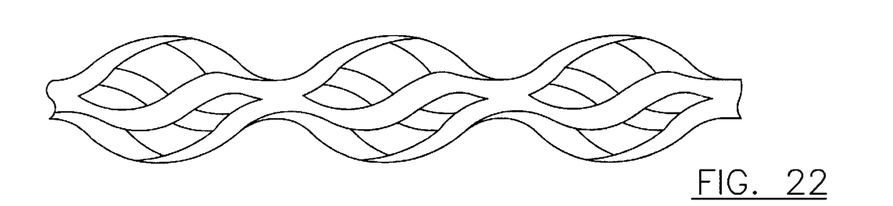
FIG. 22 is a perspective view of the ureteral device of FIG. 21 shown in an expanded state.

FIG. 21 is a perspective view of a ureteral device, in accordance with the invention, shown in a contracted state. In this embodiment, the elongate flexible members 96, 96', 96" are configured in a spiral pattern. FIG. 22 shows the ureteral device of FIG. 21 in an expanded state. In another embodiment, the members are linear or other shapes, but not parallel to the longitudinal axis of the body 88.

An exemplary method of use of the ureteral device shown in FIGS. 18–22 is described as follows. The ureteral device, in a contracted state, is guided through a ureter in a retrograde manner. This may be accomplished by using a guidewire (as described above), by guiding the device directly or by other common means of device or catheter guidance. Once the device is in a desired location in the ureter, it is induced to take an expanded state or a restraining force is removed allowing it to assume an expanded state, as described above. The natural expansion of the ureter combined with the exposed void spaces 104, 104', 104" in the device facilitate the migration of an occlusion into a void spaces. When it is determined that a target occlusion (such as a stone) has lodged in the void space of the cage, the device can be induced to take a contracted state or pulled from the ureter, thereby contracting the cages. The contracted state acts to compress and/or enclose the occlusion within the smooth body, facilitating removal. The device is then removed from the ureter along with the "captured" occlusion. It will be understood by those skilled in the art that intermediate steps may be employed in combination with those set forth here to facilitate removal of the occlusion. For example, combining a laser application step to break up the occlusion into smaller pieces may be employed. Many of the "traditional" techniques may be used in combination with the present invention as aids in the removal of the occlusion. Further, the device of the invention may be used to only expand the ureter, when such a procedure is desired.

The device described in FIGS. 18–22 is made in the following manner. A device body 88 made of a flexible tube, is either formed with apertures 98, 98', 98" along its length or the apertures are cut into the flexible tube. These apertures define the edges of the flexible members 96, 96', 96". The apertures may be of very small width, having zero tolerance, or may be expanded to form wider slots as seen in FIG. 9. It will be understood that the apertures may be formed longitudinally, non-longitudinally or in any other arrangement in accordance with the invention. Further, in one embodiment, the device is maintained in an expanded state while heat is applied to induce a shape memory effect in a material of the device. For example, if the device is constructed of silicone, it is heated to a very high temperature and allowed to cool. Upon cooling, the device will hold the expanded state when at rest. Additionally, a sheath or adhesive can then be applied to hold the device in a contracted state until use.

It will be appreciated by persons skilled in the art that the present invention is not limited to what has been particularly shown and described herein above, and that the drawings are not to scale. A variety of modifications and variations are possible in light of the above teachings without departing from the scope and spirit of the invention, which is limited only by the following claims.

What is claimed is:

1. A ureteral device comprising:
   a flexible elongate body having a first end and a second end, the flexible elongate body, in an expanded state, defining a plurality of three-dimensional cages formed by a plurality of spaced-apart members that provide a void space within each cage, at least two of the spaced apart members being spaced apart a distance sufficient to allow an occlusion to enter a void space of a cage when the elongate body is in an expanded state, the cages being generally centered about the longitudinal axis of the elongate body and being positioned between the first end and the second end, at least one of the first end and the second end being curled for anchoring at least that end within an anatomic structure.

2. The ureteral device of claim 1, wherein the cages are reversibly, radially expandable.

3. The ureteral device of claim 1, wherein the cages are defined by a plurality of elongate flexible members.

4. The ureteral device of claim 3, wherein the cages are transitionable from a contracted to an expanded state, and wherein the contracted state provides a first cage diameter and the expanded state provides a second cage diameter.

5. The ureteral device of claim 3, wherein the flexible elongate body includes a flexible tube having a body wall with an outer surface and an inner surface that defines a lumen, and wherein the plurality of elongate flexible members are defined by portions of the body wall.

6. The ureteral device of claim 5, wherein the elongate flexible members touch adjacent elongate flexible members when the plurality of cages are in a contracted state.

7. The ureteral device of claim 6, wherein the elongate flexible members are separated from each other when the plurality of cages are in an expanded state.

8. The ureteral device of claim 5, wherein the elongate flexible members are disposed in a spaced-apart relationship when the plurality of cages are in a contracted state.

9. The ureteral device of claim 3, wherein the elongate flexible members are longitudinally aligned with a longitudinal axis of the flexible elongate body.

10. The ureteral device of claim 9, wherein the elongate flexible members are defined by longitudinal apertures in the flexible elongate body.

11. The ureteral device of claim 10, wherein the longitudinal apertures are circumferentially aligned in adjacent cages.

12. The ureteral device of claim 10, wherein the longitudinal apertures are circumferentially offset in adjacent cages.

13. The ureteral device of claim 3, wherein the elongate flexible members are not longitudinally aligned with a longitudinal axis of the flexible elongate body.

14. The ureteral device of claim 3, wherein the cages are defined by two or more elongate flexible members.

15. The ureteral device of claim 3, wherein the cages are defined by three or more elongate flexible members.

16. The ureteral device of claim 1, wherein the elongate flexible body, in an expanded state, provides an undulating surface and alternating larger and smaller localized circumferential regions.

17. The ureteral device of claim 1, wherein the at least one of the first curled end and the second curled end has a curled shape memory.

18. The ureteral device of claim 1, wherein the anatomic structure comprises at least one of a bladder and a kidney.

19. The ureteral device of claim 1, wherein at least one of the first end the second end is curled to form a "J."

20. A ureteral device comprising:
    a flexible elongate body having a first end and a second end, the flexible elongate body having a plurality of elongate flexible members that are reversibly, radially expandable and provide an undulating surface of alternating larger and smaller circumferential sections to the flexible elongate body in an expanded state, at least two of the elongate flexible members, in an expanded state, defining a void space within a section, the void space being sized to receive an occlusion therein, at least one of the first end and the second end being curled for anchoring at least that end within an anatomic structure.

21. The ureteral device of claim 20, wherein the flexible elongate body is defined by two or more elongate flexible members.

22. The ureteral device of claim 20, wherein the flexible elongate body is defined by three or more elongate flexible members.

23. A ureteral device comprising:
    a flexible elongate body having a first end and a second end, the flexible elongate body having a plurality of elongate flexible members that are reversibly, radially expandable and provide an undulating surface of alternating larger and smaller circumferential sections to the flexible elongate body in a expanded state, at least two of the elongate flexible members, in an expanded state, defining a void space within a section, the void space being sized to receive an occlusion therein, the device being fabricated from a material that can degrade or dissolve.

24. The ureteral device of claim 23, wherein the material is soluble in water or urine.

25. A ureteral device comprising:

a flexible elongate body having a first end and a second end, at least one of the first end and the second end being curled for anchoring at least that end within an anatomic structure, the flexible elongate body having a plurality of elongate flexible members that are reversibly, radially expandable and provide an undulating surface of alternating larger and smaller circumferential sections to the flexible elongate body in an expanded state, at least two of the elongate flexible members, in an expanded state, defining a void space within a section, the void space being sized to receiving an occlusion therein, and a filament secured to a distal region of the flexible elongate body and extending to a proximal region of the flexible elongate body, wherein proximal displacement of the filament transitions the device to the expanded state.

26. A method of removing a ureteral obstruction, comprising the steps of:

(a) providing a device having a flexible elongate body having a first end and a second end, the flexible elongate body, in an expanded state, defining a plurality of cages between the first end and the second end;

(b) guiding the device in retrograde manner through a ureteral orifice in the bladder and through a ureter and positioning the device between a kidney and the bladder, the device being sized to extend between the kidney and the bladder;

(c) expanding the device to allow an obstruction to lodge within a cage; and (d) removing the device from the ureter.

27. The method of claim 26, wherein the cages are defined by two or more elongate flexible members.

28. The method of claim 26, wherein the cages are defined by three or more elongate flexible members.

29. The method of claim 26, wherein expanding includes permitting the ureter to dilate passively around the device.

30. The method of claim 26, wherein guiding includes guiding the device through a catheter or instrument.

31. A method of dilating a duct, comprising the steps of:

providing a device having a flexible elongate body having a first end and a second end, the flexible elongate body, in an expanded state, defining a plurality of three-dimensional cages formed by a plurality of spaced-apart members that provide a void space within each cage, at least two of the spaced apart members being spaced apart a distance sufficient to allow an occlusion to enter a void space of a cage in an expanded state, the plurality of cages being positioned between the first end and the second end;

guiding the device through a ureteral orifice in the bladder and through a ureter; and removing a contractive force to permit expansion of the plurality of cages within the ureter.

32. The method of claim 31, further comprising permitting the ureter to dilate passively around the device.

33. The method of claim 31, wherein guiding includes guiding the device through a catheter or instrument.

34. A method of making a ureteral device, comprising the steps of:

creating a plurality of apertures in a body wall of an elongate flexible body having a central lumen, the apertures penetrating a cross-section of the body wall and defining elongate flexible members in the body wall;

expanding the elongate flexible members to an expanded state, the elongate flexible members, in the expanded state, defining a plurality of three-dimensional cages, the elongate flexible members of at least one of the cages, in the expanded state, being spaced apart distance sufficient to allow an occlusion to enter a void space of the cage, curling an end of the device; and heating the elongate flexible to a temperature sufficient to induce a shape memory of the expanded state and of the curled end.

35. The method of claim 34, wherein the apertures are longitudinal slits in the body wall.

36. The method of claim 34, further comprising removing portions of the body wall adjacent to the apertures.

37. The method of claim 34, wherein the apertures are circumferentially spaced on the body wall.

* * * * *

UNITED STATES PATENT AND TRADEMARK OFFICE
CERTIFICATE OF CORRECTION

PATENT NO. : 6,709,465 B2
DATED : March 23, 2004
INVENTOR(S) : Mitchell et al.

It is certified that error appears in the above-identified patent and that said Letters Patent is hereby corrected as shown below:

<u>Column 8,</u>
Line 45, insert -- and -- after "first end".

<u>Column 9,</u>
Line 4, change "in a expanded" to -- in an expanded --.
Line 23, change "receiving" to -- receive --.
Line 36, insert -- a -- after "device in".

<u>Column 10,</u>
Line 33, insert -- a -- after "being spaced apart".
Line 37, insert -- body -- after "heating the elongate flexible".

Signed and Sealed this

Twenty-second Day of June, 2004

JON W. DUDAS
*Acting Director of the United States Patent and Trademark Office*